(12) United States Patent
Faerstein

(10) Patent No.: US 9,168,308 B2
(45) Date of Patent: Oct. 27, 2015

(54) COMPOSITIONS AND METHODS FOR NUTRITIONAL SUPPLEMENTATION

(76) Inventor: Paul Joseph Faerstein, Brooklyn, NY (US)

( * ) Notice: Subject to any disclaimer, the term of this patent is extended or adjusted under 35 U.S.C. 154(b) by 401 days.

(21) Appl. No.: 13/449,826

(22) Filed: Apr. 18, 2012

(65) Prior Publication Data

US 2012/0269868 A1    Oct. 25, 2012

Related U.S. Application Data

(60) Provisional application No. 61/478,197, filed on Apr. 22, 2011, provisional application No. 61/508,729, filed on Jul. 18, 2011, provisional application No. 61/592,905, filed on Jan. 31, 2012.

(51) Int. Cl.

| | |
|---|---|
| *A61K 31/59* | (2006.01) |
| *A61K 38/22* | (2006.01) |
| *A61K 38/43* | (2006.01) |
| *A61P 25/00* | (2006.01) |
| *A61K 9/00* | (2006.01) |
| *A61P 9/00* | (2006.01) |
| *A61P 1/16* | (2006.01) |
| *A61P 3/02* | (2006.01) |
| *A61K 31/714* | (2006.01) |
| *A61K 35/64* | (2015.01) |
| *A61K 47/44* | (2006.01) |
| *A23L 1/00* | (2006.01) |
| *A23L 1/30* | (2006.01) |
| *A23L 1/302* | (2006.01) |
| *A23L 1/303* | (2006.01) |
| *A61K 9/48* | (2006.01) |
| *A61K 47/14* | (2006.01) |
| *A61K 45/06* | (2006.01) |
| *A61K 35/60* | (2006.01) |
| *A61K 31/05* | (2006.01) |
| *A61K 31/122* | (2006.01) |
| *A61K 31/355* | (2006.01) |
| *A61K 31/4415* | (2006.01) |
| *A61K 36/185* | (2006.01) |
| *A61K 36/55* | (2006.01) |

(52) U.S. Cl.
CPC ............... *A61K 47/44* (2013.01); *A23L 1/0029* (2013.01); *A23L 1/30* (2013.01); *A23L 1/302* (2013.01); *A23L 1/303* (2013.01); *A23L 1/3006* (2013.01); *A61K 9/4825* (2013.01); *A61K 31/05* (2013.01); *A61K 31/122* (2013.01); *A61K 31/355* (2013.01); *A61K 31/4415* (2013.01); *A61K 31/59* (2013.01); *A61K 35/60* (2013.01); *A61K 36/185* (2013.01); *A61K 36/55* (2013.01); *A61K 45/06* (2013.01); *A61K 47/14* (2013.01); *A23V 2002/00* (2013.01)

(58) Field of Classification Search
None
See application file for complete search history.

(56) References Cited

U.S. PATENT DOCUMENTS

| 5,972,382 | A * | 10/1999 | Majeed et al. ................. 424/464 |
|---|---|---|---|
| 7,332,181 | B1 | 2/2008 | Habib et al. |
| 2006/0029587 | A1 * | 2/2006 | Lane ........................... 424/94.1 |
| 2008/0160077 | A1 * | 7/2008 | Borowy-Borowski ....... 424/456 |
| 2009/0004170 | A1 | 1/2009 | Ikehara et al. |
| 2009/0110674 | A1 | 4/2009 | Loizou |
| 2011/0008308 | A1 | 1/2011 | Taylor et al. |

OTHER PUBLICATIONS

International Search Report and Written Opinion dated Jul. 17, 2012 for PCT/US2012/34033.
Vagnini et al. "Preventing Pharmaceutical-induced Nutritional Deficiencies" Mar. 31, 2006, LifeExtension [online]; www.lef.org/magazine/mag2006/mar2006_report_drugs_01.htm, p. 1-11.

* cited by examiner

*Primary Examiner* — Sue Liu
*Assistant Examiner* — Erin Hirt
(74) *Attorney, Agent, or Firm* — Pepper Hamilton LLP

(57) ABSTRACT

Disclosed is a nutritional supplement composition including effective amounts of Coenzyme Q10, fish oil, vitamin D and a pharmaceutically acceptable excipient. Described is a method of promoting nutritional health comprising administering a nutritional supplement composition including Coenzyme Q10, fish oil, vitamin D and a pharmaceutically acceptable excipient to a subject. The nutritional supplement composition may further include flax seed oil, borage oil, evening primrose oil, vitamin E, resveratrol, vitamin B6, vitamin B12, folic acid, piperine and combinations. In some embodiments, administering Administering the nutritional supplement may ameliorate nutrient depletion, or promote cardiovascular health, liver health, or both. The nutritional supplement may be used to promote nutritional health taking a cholesterol lowering drug. The nutritional supplement may be used to ameliorate nutrient depletion taking a cholesterol lowering drug. The cholesterol lowering drug may be a statin.

12 Claims, No Drawings

COMPOSITIONS AND METHODS FOR NUTRITIONAL SUPPLEMENTATION

CROSS-REFERENCE TO RELATED APPLICATIONS

This application claims benefit of priority to U.S. Provisional Patent Application No. 61/478,197 filed on Apr. 22, 2011, No. 61/508,729 filed on Jul. 18, 2011, and No. 61/592,905 filed on Jan. 31, 2012, the entire contents of which are hereby incorporated by reference.

GOVERNMENT INTERESTS

Not Applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not Applicable

BRIEF SUMMARY OF THE INVENTION

Embodiments herein are directed to nutritional supplement compositions comprising an effective amount of Coenzyme Q10 and a pharmaceutically acceptable excipient. In some embodiments, the composition may further comprise effective amounts of flax seed oil and/or borage oil, evening primrose oil, vitamin D, resveratrol, fish oil, piperine, vitamin B12, vitamin E, vitamin B6, folic acid, or a combination thereof. Some embodiments describe a composition including effective amounts of Coenzyme Q10, vitamin B12, flax seed oil and/or borage oil, evening primrose oil, vitamin E, vitamin D, resveratrol and a pharmaceutically acceptable excipient. Some embodiments describe a composition including effective amounts of Coenzyme Q10, piperine, flax seed oil and/or borage oil, evening primrose oil, vitamin E, vitamin D, resveratrol and a pharmaceutically acceptable excipient. Some embodiments describe a composition including effective amounts of Coenzyme Q10, piperine, flax seed oil and/or borage oil, fish oil, evening primrose oil, vitamin E, vitamin D, resveratrol and a pharmaceutically acceptable excipient. Some embodiments describe a composition including effective amounts of Coenzyme Q10, piperine, vitamin B12, flax seed oil and/or borage oil, fish oil, evening primrose oil, vitamin E, vitamin D, resveratrol and a pharmaceutically acceptable excipient. Some embodiments describe a composition including effective amounts of Coenzyme Q10, flax seed oil and/or borage oil, fish oil, evening primrose oil, vitamin E, vitamin D, resveratrol and a pharmaceutically acceptable excipient. Some embodiments describe a composition including effective amounts of Coenzyme Q10, fish oil, vitamin E, and a pharmaceutically acceptable excipient. Some embodiments describe a composition including effective amounts of Coenzyme Q10, fish oil, resveratrol, and a pharmaceutically acceptable excipient. Some embodiments describe a composition including effective amounts of Coenzyme Q10, fish oil, vitamin D, resveratrol and a pharmaceutically acceptable excipient. Some embodiments describe a composition including effective amounts of Coenzyme Q10, vitamin B12, flax seed oil and/or borage oil, fish oil, evening primrose oil, vitamin D, resveratrol and a pharmaceutically acceptable excipient. In some embodiments, the composition may further include an effective amount of vitamin B6. In some embodiments, the composition may further include an effective amount of folic acid.

In some embodiments, a method of promoting nutritional health comprising administering a nutritional supplement composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of ameliorating nutrient depletion comprising administering a nutritional supplement composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of promoting cardiovascular health comprising administering a nutritional supplement composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of promoting liver health comprising administering a nutritional supplement composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of promoting nutritional health in a subject taking a cholesterol lowering drug comprising administering a nutritional supplement composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of ameliorating nutrient depletion in a subject taking a cholesterol lowering drug comprising administering a nutritional composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of ameliorating memory loss in a subject taking a cholesterol lowering drug comprising administering a nutritional composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of ameliorating mental confusion in a subject taking a cholesterol lowering drug comprising administering a nutritional composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

In some embodiments, a method of reducing or preventing side effects in a subject taking a cholesterol lowering drug comprising administering a nutritional composition including effective amounts of Coenzyme Q10, flax seed oil and/or borage oil, evening primrose oil, vitamin D, resveratrol and a pharmaceutically acceptable excipient to a subject in need thereof is provided. In some embodiments, the composition may further include fish oil. In some embodiments, the composition may further include piperine. In some embodiments, the composition may further include vitamin B12. In some embodiments, the composition may further include vitamin B6. In some embodiments, the composition may further include folic acid. In some embodiments, the composition may further include vitamin E.

DESCRIPTION OF DRAWINGS

Not applicable

DETAILED DESCRIPTION

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein and in the appended claims, the singular forms "a", "an", and "the" include plural reference unless the context clearly dictates otherwise. Thus, for example, reference to an "antioxidant" is a reference to one or more antioxidants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic to a patient whereby the therapeutic positively impacts the tissue to which it is targeted. Thus, as used herein, the term "administering", when used in conjunction with a nutritional supplement, can include, but is not limited to, oral or parenteral administration. Suitable forms for the nutritional supplement composition for oral or parenteral administration may include tablets, capsules, lozenges, syrups, granules, solutions and suspensions which contain unit doses of the supplement for administration once or several times a day. The nutritional supplement composition of the invention may typically be administered orally as a tablet or a capsule. Tablets, gel tabs, capsules, liquid and sustained release formulations may be formulated and prepared according to manufacturing techniques well known in the pharmaceutical industry and in a variety of dosage forms "Administering" a composition may be accomplished by oral administration, parenteral administration, or by either method in combination with other known techniques.

The term "animal," "patient," or "subject" as used herein includes, but is not limited to, humans and non-human vertebrates such as wild, domestic and farm animals. Preferably, the term refers to humans.

The term "inhibiting" includes the administration of a compound of the present invention to prevent the onset of the symptoms, alleviate the symptoms, not worsen the symptoms or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, prevent or improve an unwanted condition, disease or symptom of a patient. In part, embodiments of the present invention are directed to promoting cardiovascular health.

A "therapeutically effective amount" or "effective amount" of a composition is a predetermined amount calculated to achieve the desired effect, i.e., to supplement, promote, or increase nutritional health. The activity contemplated by the present methods includes both therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The effective amount administered may be determined by a physician in the light of the relevant circumstances including the condition to be treated, the choice of compound to be administered, and the chosen route of administration. A therapeutically effective amount of compound of this invention is typically an amount such that when it is administered in a physiologically tolerable excipient composition, it is sufficient to achieve an effective systemic concentration or local concentration in the target tissue.

The terms "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Examples of beneficial or desired clinical results may include, without limitation, normalized levels of Coenzyme Q10, increased levels of Coenzyme Q10, amelioration in depletion of Coenzyme Q10, prevention or amelioration of heart disease, prevention or amelioration of muscle pains, prevention or amelioration of muscle soreness, prevention or amelioration of muscle weakness, prevention or amelioration of diabetes, and prevention or amelioration of liver disease. The terms may further be used to convey that the disease or condition is not worsened by administration of the nutritional supplement of embodiments herein. For example, in embodiments herein, administering a nutritional supplement including Coenzyme Q10 to a subject taking statins does not worsen or deteriorate a heart condition in the subject. Amelioration or promotion includes eliciting a clinically significant response without excessive levels of side effects.

As used herein, the term "consists of" or "consisting of" means that the method, composition or formulation includes only the elements, steps, or ingredients specifically recited in the particular claimed embodiment or claim.

As used herein, the term "consisting essentially of" or "consists essentially of" means that method, composition or formulation includes only the elements, steps or ingredients specifically recited in the particular claimed embodiment or claim and, optionally, elements, steps or ingredients that do not materially affect the basic and novel characteristics of the particular method composition or formulation in the particular embodiment or claim.

Generally speaking, the term "tissue" refers to any aggregation of similarly specialized cells which are united in the performance of a particular function.

In some aspects, the invention is directed to compositions comprising a nutritional supplement and a pharmaceutically acceptable carrier, a diluent or combinations thereof. In some embodiments, the invention is directed to compositions comprising an effective amount of a nutritional supplement, as disclosed herein.

Cholesterol lowering drugs, such as statins, may reduce the production of Coenzyme Q10, which is a safe antioxidant that promotes a healthy heart and liver in the body, and cause many serious health risks. Beta blockers or beta-adrenergic blocking agents, beta-adrenergic antagonists, or beta antagonists are a class of drugs used for various indications, but particularly for the management of cardiac arrhythmias, cardioprotection after myocardial infarction, and hypertension. Without wishing to be bound by theory, it is believed that the synthesis of an intermediary precursor of coenzyme Q10, mevalonate, is inhibited by the use of some beta blockers, blood pressure-lowering medication, and statins. Statins include, but are not limited to, lovastatin, atorvastatin, rosuvastatin, fluvastatin, pitavastatin, pravastatin and simvastatin.

Coenzyme Q10, also known as "CoQ10," is a component of the electron transport chain and participates in aerobic cellular respiration, generating energy in the form of ATP. About ninety-five percent of the human body's energy is generated through this pathway. Therefore, those organs with the highest energy requirements such as the heart, liver and kidney may have the highest CoQ10 concentrations. Coenzyme Q10 exists in three redox states—fully oxidized (ubiquinone), partially reduced (semiquinone or ubisemiquinone) and fully reduced (ubiquinol). The ubiquinone form of Coenzyme Q10 is a 1,4-benzoquinone, where Q refers to the quinone chemical group and 10 refers to the number of isoprenyl chemical subunits in its tail. Semiquinone (or ubisemiquinone) is a free radical resulting from the removal of one hydrogen atom with its electron during the process of dehydrogenation of a hydroquinone to quinone or alternatively the addition of a single H atom to a quinone. Ubiquinol is an electron-rich (reduced) form of coenzyme Q10. The natural ubiquinol form of Coenzyme Q10 is 2,3-dimethoxy-5-methyl-6-poly prenyl-1,4-benzoquinol, where the polyprenylated side chain is 9-10 units long in mammals.

Without wishing to be bound in theory, a reduction of Coenzyme Q10 may impair even the most basic physiological functions. For example, a reduction in Coenzyme Q10 may cause heart disease, liver disease, muscle soreness and weakness. For individuals taking statins, beta-blockers or blood pressure lowering drugs, a reduction of Coenzyme Q10 caused by the drug may actually cause a worsening of the heart condition being treated. Without wishing to be bound by theory, it is believed that a subject taking such drugs will not only have reduced Coenzyme Q10 but may also be deficient in, without limitation, vitamin D, vitamin E, healthy cholesterol, and omega-3, 6 and 9 fatty acids. Without wishing to be bound by theory, it is believed that a subject taking a cholesterol lowering drug may experience side effects including constipation, nausea, peripheral neuropathy, depression, diabetes, muscle pain, muscle cramping, joint pain, mental confusion, memory loss, and liver damage.

Accordingly, there is a need for a nutritional supplement containing Coenzyme Q10, vitamins D and E, and healthy cholesterol for the prevention of Coenzyme Q10 depletion; prevention of heart disease, diabetes, muscle pains, muscle soreness, muscle weakness and liver disease; and promotion of cardiovascular and liver health. Furthermore, the inclusion of resveratrol in such nutritional supplement promotes healthy heart and cardiovascular system. Such nutritional supplements may be especially useful for individuals taking a cholesterol lowering drug.

Embodiments herein are directed to a nutritional supplement composition comprising Coenzyme Q10 and a pharmaceutically acceptable excipient. In some embodiments, the composition may further comprise flax seed oil and/or borage oil, evening primrose oil, vitamin D, resveratrol, fish oil, piperine, vitamin B12, vitamin E, vitamin B6, folic acid, or a combination thereof. Some embodiments are directed to a nutritional supplement composition comprising Coenzyme Q10, flax seed oil and/or borage oil, fish oil, evening primrose oil, vitamin E, vitamin D, resveratrol and a pharmaceutically acceptable excipient. Some embodiments are directed to a nutritional supplement composition comprising Coenzyme Q10, flax seed oil and/or borage oil, piperine, evening primrose oil, vitamin E, vitamin D, resveratrol and a pharmaceutically acceptable excipient. Some embodiments are directed to a nutritional supplement composition comprising Coenzyme Q10, flax seed oil and/or borage oil, vitamin B12, evening primrose oil, vitamin E, vitamin D, resveratrol and a pharmaceutically acceptable excipient. Some embodiments are directed to a nutritional supplement composition comprising Coenzyme Q10, flax seed oil and/or borage oil, piperine, vitamin B12, evening primrose oil, vitamin E, vitamin D, resveratrol and a pharmaceutically acceptable excipient. Some embodiments are directed to a nutritional supplement composition comprising Coenzyme Q10, flax seed oil and/or borage oil, fish oil, piperine, vitamin B12, evening primrose oil, vitamin E, vitamin D, resveratrol and a pharmaceutically acceptable excipient. Some embodiments describe a composition including Coenzyme Q10, fish oil, vitamin E, and a pharmaceutically acceptable excipient. Some embodiments describe a composition including Coenzyme Q10, fish oil, resveratrol, and a pharmaceutically acceptable excipient. Some embodiments describe a composition including Coenzyme Q10, fish oil, vitamin D, resveratrol and a pharmaceutically acceptable excipient. Some embodiments describe a composition including Coenzyme Q10, vitamin B12, flax seed oil and/or borage oil, fish oil, evening primrose oil, vitamin D, resveratrol and a pharmaceutically acceptable excipient. In some embodiments, the composition may further include vitamin B6. In some embodiments, the composition may further include folic acid. In some embodiments, the nutritional supplement composition contains an amount of each ingredient that is compatible with the other ingredients in the formulation. In some embodiments, the nutritional supplement composition contains an amount of each ingredient so that the ingredient retains its efficacy in the human body when combined with the other ingredients in the formulation. Some embodiments are directed to a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient. Some embodiments are directed to a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient.

Embodiments herein are directed to a nutritional supplement composition comprising Coenzyme Q10, fish oil, vitamin D and a pharmaceutically acceptable excipient. In some embodiments, the composition may further comprise flax seed oil and/or borage oil, evening primrose oil, resveratrol, piperine, vitamin B12, vitamin E, vitamin B6, folic acid, or a combination thereof. In some embodiments, the nutritional supplement composition comprises Coenzyme Q10, fish oil, vitamin D, flax seed oil and/or borage oil, evening primrose oil, vitamin E, resveratrol and a pharmaceutically acceptable excipient. In some embodiments, the nutritional supplement composition comprises Coenzyme Q10, fish oil, vitamin D, flax seed oil and/or borage oil, piperine, evening primrose oil, vitamin E, resveratrol and a pharmaceutically acceptable excipient. In some embodiments, the nutritional supplement composition comprises Coenzyme Q10, fish oil, vitamin D, vitamin B12, evening primrose oil, vitamin E, resveratrol and a pharmaceutically acceptable excipient. In some embodiments, the nutritional supplement composition comprises Coenzyme Q10, fish oil, piperine, vitamin B12, evening primrose oil, vitamin E, vitamin D, resveratrol and a pharmaceutically acceptable excipient. In some embodiments, the nutritional supplement composition comprises Coenzyme Q10, fish oil, vitamin D, flax seed oil and/or borage oil, piperine, vitamin B12, evening primrose oil, vitamin E, resveratrol and a pharmaceutically acceptable excipient. Some embodiments describe a composition including Coenzyme Q10, fish oil, vitamin D, vitamin E, and a pharmaceutically acceptable excipient. Some embodiments describe a composition including Coenzyme Q10, fish oil, vitamin D, resveratrol and a pharmaceutically acceptable excipient. Some embodiments describe a composition including Coenzyme Q10, fish oil, vitamin D, resveratrol and a pharmaceutically acceptable excipient. Some embodiments describe a composition including Coenzyme Q10, fish oil, vitamin D, vitamin B12, flax seed oil and/or borage oil, evening primrose oil, resveratrol and a pharmaceutically acceptable excipient. In some embodiments, the composition may further include vitamin B6, folic acid or a combination thereof. In some embodiments, the nutritional supplement composition contains an amount of each ingredient that is compatible with the other ingredients in the formulation. In some embodiments, the nutritional supplement composition contains an amount of each ingredient so that the ingredient retains its efficacy in the human body when combined with the other ingredients in the formulation. Some embodiments are directed to a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient. Some embodiments are directed to a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient.

In some embodiments, a method of promoting nutritional health comprising administering to a subject in need thereof, a nutritional supplement composition comprising Coenzyme Q10, flax seed oil and/or borage oil, evening primrose oil, vitamin D, resveratrol and a pharmaceutically acceptable excipient is provided. In some embodiments, a method of promoting nutritional health comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting nutritional health comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of promoting nutritional health comprising administering to a subject in need thereof, a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, vitamin E, flax seed oil and/or borage oil, evening primrose oil, resveratrol or combinations thereof. In some embodiments, a method of promoting nutritional health comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting nutritional health comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of promoting cardiovascular health comprising administering to a subject in need thereof, a nutritional supplement composition comprising Coenzyme Q10, flax seed oil and/or borage oil, evening primrose oil, vitamin D, resveratrol and a pharmaceutically acceptable excipient is provided. In some embodiments, a method of promoting cardiovascular health comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting cardiovascular health comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of promoting cardiovascular health comprising administering to a subject in need thereof, a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, folic acid, vitamin E, flax seed oil and/or borage oil, evening primrose oil, resveratrol or a combination thereof. In some embodiments, a method of promoting cardiovascular health comprising administering to a subject in need thereof, a nutritional supplement composition consisting essentially of Coenzyme Q10, fish oil, vitamin D, flax seed oil and/or borage oil, evening primrose oil, resveratrol, vitamin B6, vitamin E, folic acid, vitamin B12, piperine and a pharmaceutically acceptable excipient is provided. In some embodiments, a method of promoting cardiovascular health comprising administering to a subject in need thereof, a nutritional supplement composition consisting of Coenzyme Q10, fish oil, vitamin D, flax seed oil and/or borage oil, evening primrose oil, resveratrol, vitamin B6, vitamin E, folic acid, vitamin B12, piperine and a pharmaceutically acceptable excipient is provided.

In some embodiments, a method of promoting liver health comprising administering to a subject in need thereof, a nutritional supplement composition comprising Coenzyme Q10, flax seed oil and/or borage oil, evening primrose oil, vitamin D, resveratrol and a pharmaceutically acceptable excipient is provided. In some embodiments, a method of promoting liver health comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting liver health comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of promoting liver health comprising administering to a subject in need thereof, a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, folic acid, vitamin E, flax seed oil and/or borage oil, primrose oil, include resveratrol or a combination thereof. In some embodiments, a method of promoting liver health comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting liver health comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of promoting nutritional health in a subject taking a cholesterol lowering drug comprising administering a nutritional supplement composition comprising Coenzyme Q10, flax seed oil and/or borage oil, evening primrose oil, vitamin D, resveratrol and a pharmaceutically acceptable excipient is provided. In some embodiments, a method of promoting nutritional health in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting nutritional health in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of promoting nutritional health in a subject taking a cholesterol lowering drug comprising administering a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, folic acid, vitamin E, flax seed oil and/or borage oil, primrose oil, include resveratrol or a combination thereof. In some embodiments, a method of promoting nutritional health in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of promoting nutritional health in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of ameliorating nutrient depletion in a subject taking a cholesterol lowering drug comprising administering a nutritional supplement composition comprising Coenzyme Q10, flax seed oil and/or borage oil, evening primrose oil, vitamin D, resveratrol and a pharmaceutically acceptable excipient is provided. In some embodiments, the cholesterol lowering drug may be a statin. In some embodiments, a method of ameliorating nutrient depletion in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating nutrient depletion in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of ameliorating nutrient depletion in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of ameliorating nutrient depletion in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating nutrient depletion in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, the compositions described herein may be used for the alleviation of early stage heart failure. Heart failure, commonly referred to as congestive heart failure, is the heart's inability to sufficiently fill with the blood or the heart's inability to distribute a sufficient amount of blood throughout the body. The American College of Cardiology categorizes heart failure into four stages. The first stage, Stage A, is a stage in which there are no symptoms at any level of exertion and the heart is structurally normal. However, the subject may be at risk for developing heart failure. Stage B is where the heart may have structural defects and the subject may experience mild or no symptoms. Stage C heart failure is where there is cardiac dysfunction and symptoms of heart failure are present, including, for example, shortness of breath, tiredness when doing simple activities, or overall fatigue. Stage D heart failure is severe heart failure and symptoms may be present during minimal activity or at rest. Early stage heart failure commonly includes Stage A and Stage B heart failure. Ejection fraction (Ef) is the fraction of blood pumped out of the right and left ventricles with each heart beat. In patients with heart failure, the ejection fraction may be dramatically reduced.

In some embodiments, a method of alleviating early stage heart failure comprises administrating a nutritional supplement composition comprising Coenzyme Q10, flax seed oil and/or borage oil, fish oil, evening primrose oil, vitamin E, vitamin D, resveratrol and a pharmaceutically acceptable excipient. In some embodiments, a method of promoting reversal of early stage heart failure comprises administrating a nutritional supplement composition comprising Coenzyme Q10, flax seed oil and/or borage oil, fish oil, evening primrose oil, vitamin E, vitamin D, resveratrol and a pharmaceutically acceptable excipient. In some embodiments, a method for normalizing the heart size comprises administrating a nutritional supplement composition comprising Coenzyme Q10, flax seed oil and/or borage oil, fish oil, evening primrose oil, vitamin E, vitamin D, resveratrol and a pharmaceutically acceptable excipient. Some embodiments describe a method of increasing ejection fraction of the ventricles comprising administering a nutritional supplement composition comprising Coenzyme Q10, flax seed oil and/or borage oil, fish oil, evening primrose oil, vitamin E, vitamin D, resveratrol and a pharmaceutically acceptable excipient to a subject in need thereof. In some embodiments, the nutritional supplement composition may also include vitamin B12, piperine or a combination thereof. In some embodiments, early stage heart failure includes Stage A heart failure, Stage B heart failure or a combination thereof. In some embodiments, administering the nutritional supplement composition is in conjunction with a therapeutic drug. In some embodiments, the therapeutic drug may comprise an anti-hypertensive drug. In some embodiments, the anti-hypertensive drug may include thiazide diuretics, angiotensin-converting enzyme (ACE) inhibitors, calcium channel blockers, beta blockers, angiotensin II receptor antagonists (ARBs) or a combination thereof. Without wishing to be bound by theory, it is believed that the concomitant use of the nutritional supplement composition of embodiments described herein with an anti-hypertensive therapeutic drug may reverse early stage heart failure. In some embodiments, administration of an anti-hypertensive drug in conjunction with a nutritional supplement composition of embodiments herein may normalize the size of the heart.

In some embodiments, a method of alleviating early stage heart failure comprises administrating a nutritional supplement composition consisting essentially of Coenzyme Q10, flax seed oil and/or borage oil, fish oil, evening primrose oil, vitamin E, vitamin D, resveratrol and a pharmaceutically acceptable excipient. In some embodiments, a method of promoting reversal of early stage heart failure comprises administrating a nutritional supplement composition consisting essentially of Coenzyme Q10, flax seed oil and/or borage oil, fish oil, evening primrose oil, vitamin E, vitamin D, resveratrol and a pharmaceutically acceptable excipient. Some embodiments describe a method of increasing ejection fraction of the ventricles comprising administering a nutritional supplement composition consisting essentially of Coenzyme Q10, flax seed oil and/or borage oil, fish oil, evening primrose oil, vitamin E, vitamin D, resveratrol and a pharmaceutically acceptable excipient to a subject in need thereof. In some embodiments, the nutritional supplement composition also includes vitamin B12, piperine or a combination thereof.

In some embodiments, a method of alleviating early stage heart failure comprises administrating a nutritional supplement composition consisting of Coenzyme Q10, flax seed oil and/or borage oil, fish oil, evening primrose oil, vitamin E, vitamin D, resveratrol and a pharmaceutically acceptable excipient. In some embodiments, a method of promoting reversal of early stage heart failure comprising administrating a nutritional supplement composition consisting of Coenzyme Q10, flax seed oil and/or borage oil, fish oil, evening primrose oil, vitamin E, vitamin D, resveratrol and a pharmaceutically acceptable excipient is described. Some embodiments describe a method of increasing ejection fraction of the ventricles comprising administering a nutritional supplement composition consisting of Coenzyme Q10, flax seed oil and/or borage oil, fish oil, evening primrose oil, vitamin E, vitamin D, resveratrol and a pharmaceutically acceptable excipient to a subject in need thereof. In some embodiments, the nutritional supplement composition also includes vitamin B12, piperine or a combination thereof.

In some embodiments, a method of alleviating early stage heart failure comprising administering to a subject in need thereof, a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, folic acid, vitamin E, flax seed oil and/or borage oil, evening primrose oil, resveratrol or a combination thereof. In some embodiments, a method of alleviating early stage heart failure comprising administering to a subject in need thereof, a nutritional supplement composition consisting essentially of Coenzyme Q10, fish oil, vitamin D, flax seed oil and/or borage oil, evening primrose oil, resveratrol, vitamin B6, vitamin E, folic acid, vitamin B12, piperine and a pharmaceutically acceptable excipient is provided. In some embodiments, a method of alleviating early stage heart failure comprising administering to a subject in need thereof, a nutritional supplement composition consisting of Coenzyme Q10, fish oil, vitamin D, flax seed oil and/or borage oil, evening primrose oil, resveratrol, vitamin B6, vitamin E, folic acid, vitamin B12, piperine and a pharmaceutically acceptable excipient is provided.

In some embodiments, a method of ameliorating memory loss in a subject taking a cholesterol lowering drug comprising administering a nutritional supplement composition comprising Coenzyme Q10, flax seed oil and/or borage oil, evening primrose oil, vitamin D, resveratrol and a pharmaceutically acceptable excipient is provided. In some embodiments, the cholesterol lowering drug may be a statin. In some embodiments, a method of ameliorating memory loss in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating memory loss in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of ameliorating memory loss in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol or a combination thereof. In some embodiments, a method of ameliorating memory loss in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating memory loss in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of ameliorating mental confusion in a subject taking a cholesterol lowering drug comprising administering a nutritional supplement composition comprising Coenzyme Q10, flax seed oil and/or borage oil, evening primrose oil, vitamin D, resveratrol and a pharmaceutically acceptable excipient is provided. In some embodiments, the cholesterol lowering drug may be a statin. In some embodiments, a method of ameliorating mental confusion in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating mental confusion in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of ameliorating mental confusion in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of ameliorating mental confusion in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of ameliorating mental confusion in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of reducing or preventing the side effects in a subject taking a cholesterol lowering drug comprising administering a nutritional supplement composition comprising Coenzyme Q10, flax seed oil and/or borage oil, evening primrose oil, vitamin D, resveratrol and a pharmaceutically acceptable excipient is provided. The side effects of cholesterol lowering drugs may include constipation, nausea, peripheral neuropathy, depression, diabetes, muscle pain, muscle cramping, joint pain, mental confusion, memory loss, and liver damage. In some embodiments, the cholesterol lowering drug may be a statin. In some embodiments, a method of reducing or preventing side effects in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of reducing or preventing side effects in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In each of the foregoing embodiments, the composition may further include fish oil. In each of the foregoing embodiments, the composition may further include piperine. In each of the foregoing embodiments, the composition may further include vitamin B12. In each of the foregoing embodiments, the composition may further include vitamin B6. In each of the foregoing embodiments, the composition may further include folic acid. In each of the foregoing embodiments, the composition may further include vitamin E.

In some embodiments, a method of reducing or preventing the side effects in a subject taking a cholesterol lowering drug comprising administering a nutritional supplement composition comprising Coenzyme Q10, fish oil, vitamin D and a pharmaceutically acceptable excipient is provided. The side effects of cholesterol lowering drugs may include constipation, nausea, peripheral neuropathy, depression, diabetes, muscle pain, muscle cramping, joint pain, mental confusion, memory loss, and liver damage. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of reducing or preventing side effects in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of reducing or preventing side effects in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of providing cardiac protection in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of providing cardiac protection in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of providing cardiac protection in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of improving peripheral neuropathy in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of improving peripheral neuropathy in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of improving peripheral neuropathy in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of relieving muscle or joint pain in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of relieving muscle or joint pain in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of relieving muscle or joint pain in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of preventing thrombosis comprising administering to a subject in need thereof, a nutritional supplement composition comprising Coenzyme Q10, fish oil, vitamin D and a pharmaceutically acceptable excipient is provided. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of preventing thrombosis comprising administering to a subject in need thereof, a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of preventing thrombosis comprising administering to a subject in need thereof, a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of preventing exercise intolerance in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of preventing exercise intolerance in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of preventing exercise intolerance in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, a method of preventing myoglobinuria in a subject taking a cholesterol lowering drug comprising administering a nutritional supplement composition comprising Coenzyme Q10, fish oil, vitamin D and a pharmaceutically acceptable excipient is provided. In some embodiments, the cholesterol lowering drug may be a statin. In each of the foregoing embodiments, the composition may further include piperine, vitamin B12, vitamin B6, folic acid, vitamin E, flax seed oil and/or borage oil, evening primrose oil, resveratrol, or a combination thereof. In some embodiments, a method of preventing myoglobinuria in a subject taking a cholesterol lowering drug comprising administering a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided. In some embodiments, a method of preventing myoglobinuria in a subject taking a cholesterol lowering drug comprising administering a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient is provided.

In some embodiments, the nutritional supplement may include Coenzyme Q10. In some embodiments, the Coenzyme Q10 may be ubiquinol or ubiquinone. In some embodiments, the Coenzyme Q10 may be present in an effective amount from about 1 to about 2000 mg. In some embodiments, the Coenzyme Q10 may be present in an amount from about 1 mg to about 500 mg, from about 1 mg to about 300 mg, from about 1 mg to about 100 mg, from about 10 mg to about 1000 mg, from about 50 mg to about 1000 mg, from about 100 mg to about 1000 mg, from about 10 mg to about 2000 mg, from about 50 mg to about 2000 mg, from about 100 mg to about 2000 mg, from about 10 mg to about 500 mg, from about 50 mg to about 500 mg, from about 100 mg to about 500 mg, from about 10 mg to about 300 mg, from about 50 mg to about 300 mg, from about 100 mg to about 300 mg, from about 10 mg to about 150 mg, from about 50 mg to about 150 mg, about 60 mg to about 120 mg, about 50 mg to about 120 mg or a range between any two values therein. Specific examples include, for example, about 1000 mg, about 500 mg, about 300 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg and the like.

Flaxseed oil may aid in preventing heart disease, arthritis, and inflammatory bowel disease. Flaxseed oil includes omega-3 essential fatty acid, which, without wishing to be bound by theory, may reduce cholesterol, kill certain types of cancer cells, and prevent skin problems such as eczema and acne. Furthermore, it may be beneficial for subjects with sensitive stomachs because it targets excess stomach acids, sooths ulcers, and absorbs toxins. In addition to essential fatty acids, flaxseed oil also contains fibers, proteins, and lignans. Without wishing to be bound by theory, it is believed that lignans may have antioxidant properties that fight against viruses, bacteria, and cancer. In some embodiments, the nutritional supplement may comprise flaxseed oil. In some embodiments, the flaxseed oil may be present in an effective amount from about 1 mg to about 1000 mg, about 10 mg to about 1000 mg, about 50 mg to about 1000 mg, about 100 mg to about 1000 mg, about 150 mg to about 1000 mg, about 200 mg to about 1000 mg, about 250 mg to about 1000 mg, about 300 mg to about 1000 mg, about 400 mg to about 1000 mg, about 1 mg to about 500 mg, about 10 mg to about 500 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 400 mg to about 500 mg, about 1 mg to about 400 mg, about 10 mg to about 400 mg, about 50 mg to about 400 mg, about 100 mg to about 400 mg, about 150 mg to about 400 mg, about 200 mg to about 400 mg, about 250 mg to about 400 mg, about 300 mg to about 400 mg, or a range between any two values therein. Specific examples include, for example, about 100 mg, about 200 mg, about 250 mg, about 300 mg, about 350 mg, about 400 mg, about 450 mg, about 500 mg or the like.

Fish oil may be beneficial for the cardiovascular system because it contains omega-3 fatty acids that may lower cholesterol serum and triglyceride levels in the blood. Eicosapentaenoic acid (EPA), a type of omega-3 fatty acid, makes the blood thinner and less likely to clump or clot. Without wishing to be bound by theory, it is believed that EPA may reduce the chance of stroke, heart attack, heart disease, and may improve overall heart health. Docosahexaenoic acid (DHA), an omega-3 fatty acid, is the most abundant fatty acid in the brain and retina. Without wishing to be bound by theory, it is believed that a deficiency in DHA levels may be linked to memory loss and mental confusion. EPA and DHA may also benefit the health of joints, bones, kidney, liver, lungs, teeth, eyes, or a combination thereof. In some embodiments, the nutritional supplement may include fish oil. In some embodiments, the fish oil comprises eicosapentaenoic acid (EPA), docosahexaenoic acid (DHA), other omega-3 fatty acids, or a combination thereof. In some embodiments, fish oil may comprise a ratio of EPA to DHA in an effective amount of about 1.5:1 to about 2:1, about 1:1 to about 2:1, about 1.3:1 to about 2:1, 1.5:1 to about 3:1, about 1:1 to about 3:1, about 1.3:1 to about 3:1, or a range between any two values therein. Specific examples may include, for example, about 1:1, about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1 and the like. For example, in some embodiments, the nutritional supplement may include about 1200 mg of EPA to about 600 mg of DHA, about 1200 mg of EPA to about 400 mg of DHA, about 1800 mg of EPA to about 600 mg of DHA, about 1800 mg of EPA to about 900 mg of DHA, about 2000 mg of EPA to about 1000 mg of DHA, about 600 mg of EPA and about 200 mg of DHA, about 500 mg of EPA and about 200 mg of DHA, about 400 mg of EPA and about 200 mg of DHA, about 300 mg of EPA and about 200 mg of DHA, about 250 mg of EPA and about 150 mg of DHA, about 250 mg of EPA and about 200 mg of DHA, or about 300 mg of EPA and about 250 mg of DHA, or about 180 mg of EPA and about 120 mg of DHA. In some embodiments, the nutritional supplement composition may include DHA in an amount from about 1 mg to about 1000 mg, about 50 mg to about 1000 mg, about 75 mg to about 1000 mg, about 100 mg to about 1000 mg, about 150 mg to about 1000 mg, about 200 mg to about 1000 mg, about 250 mg to about 1000 mg, about 300 mg to about 1000 mg, about 50 mg to about 500 mg, about 75 mg to about 500 mg, about 100 mg to about 500 mg, about 150 mg to about 500 mg, about 200 mg to about 500 mg, about 250 mg to about 500 mg, about 300 mg to about 500 mg, about 50 mg to about 300 mg, about 75 mg to about 300 mg, about 100 mg to about 300 mg, about 150 mg to about 300 mg, about 200 mg to about 300 mg, about 250 mg to about 300 mg, or a range between any two of these values. In some embodiments, the nutritional supplement may include about 50 mg, about 100 mg, about 150 mg, about 175 mg, about 200 mg, about 250 mg, or about 300 mg of DHA. In some embodiments, the nutritional supplement composition may include EPA in an amount from about 1 mg to about 1000 mg, about 50 mg to about 1000 mg, about 75 mg to about 1000 mg, about 100 mg to about 1000 mg, about 150 mg to about 1000 mg, about 200 mg to about 1000 mg, about 250 mg to about 1000 mg, about 300 mg to about 1000 mg, about 50 mg to about 500 mg, about 75 mg to about 500 mg, about 100 mg to about 500 mg, about 150 mg to about 500 mg, about 200 mg to about 500 mg, about 250 mg to about 500 mg, about 300 mg to about 500 mg, about 50 mg to about 300 mg, about 75 mg to about 300 mg, about 100 mg to about 300 mg, about 150 mg to about 300 mg, about 200 mg to about 300 mg, about 250 mg to about 300 mg, or a range between any two of these values. In some embodiments, the nutritional supplement may include about 150 mg, about 200 mg, about 300 mg, about 350 mg, about 400 mg, about 450 mg, about 500 mg or about 600 mg of EPA. In some embodiments, the fish oil may be present in an effective amount from about 1 mg to about 1500 mg, about 10 mg to about 1250 mg, about 50 mg to about 1000 mg, about 100 mg to about 1000 mg, about 150 mg to about 1000 mg, about 200 mg to about 1000 mg, about 250 mg to about 1000 mg, about 300 mg to about 1000 mg, about 1 mg to about 500 mg, about 10 mg to about 500 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 1 mg to about 300 mg, about 10 mg to about 300 mg, about 50 mg to about 300 mg, about 100 mg to about 300 mg, about 150 mg to about 300 mg, about 200 mg to about 300 mg, about 250 mg to about 300 mg, or a range between any two values therein. Specific examples include, for example, about 1250 mg, about 1000 mg, about 900 mg, about 750 mg, about 600 mg, about 550 mg, about 525 mg, about 500 mg, about 450 mg, about 100 mg, about 150 mg, about 200 mg, about 250 mg, about 300 mg, or the like. Fish oil may comprise omega-3 fatty acids other than DHA or EPA. In some embodiments, the nutritional supplement composition may include omega-3 fatty acids in an amount from about 50 mg to about 1000 mg, about 75 mg to about 1000 mg, about 100 mg to about 1000 mg, about 150 mg to about 1000 mg, about 200 mg to about 1000 mg, about 250 mg to about 1000 mg, about 300 mg to about 1000 mg, about 50 mg to about 500 mg, about 75 mg to about 500 mg, about 100 mg to about 500 mg, about 150 mg to about 500 mg, about 200 mg to about 500 mg, about 250 mg to about 500 mg, about 300 mg to about 500 mg, about 50 mg to about 300 mg, about 75 mg to about 300 mg, about 100 mg to about 300 mg, about 150 mg to about 300 mg, about 200 mg to about 300 mg, about 250 mg to about 300 mg, or a range between any two of these values. For example, in some embodiments, the nutritional supplement may include about 200 mg, about 300 mg, about 350 mg, about 375 mg, about 400 mg, about 450 mg, or about 500 mg of omega-3 fatty acids.

Evening primrose oil is an extract of the evening primrose and includes essential fatty acids, such as cis-linoleic acid, gamma linoleic acid, and oleic acid. It may be used to help maintain a healthy heart, treat inflammatory problems such as arthritis, relieve skin problems such as eczema, treat joint pain, sooth pre-menstrual syndrome (PMS) symptoms, and improve hair, skin and nail health. In some embodiments, the nutritional supplement comprises evening primrose oil. In some embodiments, the evening primrose oil is present in an effective amount from about 1 mg to about 10,000 mg, about 100 mg to about 10000 mg, about 200 mg to about 10000 mg, about 250 mg to about 10000 mg, about 300 mg to about 10000 mg, about 400 mg to about 10000 mg, about 500 mg to about 10000 mg, about 1 mg to about 5000 mg, about 100 mg to about 5000 mg, about 200 mg to about 5000 mg, about 250 mg to about 5000 mg, about 300 mg to about 5000 mg, about 400 mg to about 5000 mg, about 500 mg to about 5000 mg, about 10 mg to about 1000 mg, about 50 mg to about 1000 mg, about 150 mg to about 1000 mg, about 200 mg to about 1000 mg, about 250 mg to about 1000 mg, about 300 mg to about 1000 mg, about 400 mg to about 1000 mg, about 1 mg to about 500 mg, about 150 mg to about 500 mg, about 200 mg to about 500 mg, about 250 mg to about 500 mg, about 300 mg to about 500 mg, about 400 mg to about 500 mg, about 1 mg to about 4000 mg, about 10 mg to about 4000 mg, about 50 mg to about 4000 mg, about 1000 mg to about 4000 mg, about 1500 mg to about 4000 mg, about 2000 mg to about 4000 mg, about 2500 mg to about 4000 mg, about 3000 mg to about 4000 mg, or a range between any two values therein. Specific examples include, for example, about 100 mg, about 150 mg, about 200 mg, about 250 mg, about 300 mg, about 350 mg, about 400 mg, about 450 mg, about 500 mg, about 1000 mg, about 1500 mg, about 2000 mg, about 3000 mg, about 4000 mg, about 5000 mg or the like.

Vitamin E is used to refer to a group of fat-soluble compounds that include both tocopherols and tocotrienols. Vitamin E helps fight off free radicals and supports a healthy immune system, and cardiovascular, circulatory, prostate, and metabolic health. In some embodiments, vitamin E may include α-tocopherol, β-tocopherol, γ-tocopherol, δ-tocopherol, α-tocotrienol, tocotrienol, γ-tocotrienol, δ-tocotrienol or a combination thereof. In some embodiments, vitamin E may include α-tocopherol, γ-tocopherol, α-tocotrienol, β-tocotrienol, γ-tocotrienol, δ-tocotrienol or a combination thereof. In some embodiments, vitamin E may include a mixture of tocotrienols. In some embodiments, the vitamin E may be natural vitamin E. In some embodiments, the vitamin E may be synthetic vitamin E. In some embodiments, the nutritional supplement comprises vitamin E. In some embodiments, the vitamin E is present in an effective amount from about 1 International Unit (IU) to about 1000 IU, about 10 IU to about 1000 IU, about 20 IU to about 1000 IU, about 30 IU to about 1000 IU, about 40 IU to about 1000 IU, about 1 IU to about 500 IU, about 10 IU to about 500 IU, about 20 IU to about 500 IU, about 30 IU to about 500 IU, about 40 IU to about 500 IU, about 1 IU to about 250 IU, about 10 IU to about 250 IU, about 20 IU to about 250 IU, about 30 IU to about 250 IU, about 40 IU to about 250 IU, about 1 IU to about 100 IU, about 10 IU to about 100 IU, about 20 IU to about 100 IU, about 30 IU to about 100 IU, about 40 IU to about 100 IU, about 1 IU to about 50 IU, about 10 IU to about 50 IU, about 20 IU to about 50 IU, about 30 IU to about 50 IU, about 40 IU to about 50 IU, or a range between any two values therein. Specific examples include, for example, about 10 IU, about 15 IU, about 20 IU, about 25 IU, about 30 IU, about 35 IU, about 40 IU or the like.

Vitamin D is a group of fat-soluble secosteroids whose main biologic function is to maintain normal levels of calcium and phosphorus in the blood. Vitamin D aids in the absorption of calcium in order to help build strong bones. A lack of vitamin D can result in skeletal deformities as well as muscular weakness. Furthermore, without wishing to be bound by theory, it is believed that vitamin D supplements may also help prevent osteoporosis, high blood pressure, cancer, and other diseases. In some embodiments, vitamin D comprises vitamin D1, vitamin D2, vitamin D3, vitamin D4, vitamin D5 or a combination thereof. In some embodiments, vitamin D comprises vitamin D2, vitamin D3, or a combination thereof. In some embodiments, the nutritional supplement comprises vitamin D. In some embodiments, the vitamin D is present in an effective amount from about 1 International Unit (IU) to about 40,000 IU, about 100 IU to about 40,000 IU, about 250 IU to about 40,000 IU, about 500 IU to about 40,000 IU, about 750 IU to about 40,000 IU, about 1000 IU to about 40,000 IU, about 100 IU to about 20,000 IU, about 250 IU to about 20,000 IU, about 500 IU to about 20,000 IU, about 750 IU to about 20,000 IU, about 1000 IU to about 20,000 IU, about 100 IU to about 10,000 IU, about 250 IU to about 10,000 IU, about 500 IU to about 10,000 IU, about 750 IU to about 10,000 IU, about 1000 IU to about 10,000 IU, about 1 IU to about 5000 IU, about 100 IU to about 5000 IU, about 250 IU to about 5000 IU, about 500 IU to about 5000 IU, about 750 IU to about 5000 IU, about 1000 IU to about 5000 IU, about 1 IU to about 2500 IU, about 100 IU to about 2500 IU, about 250 IU to about 2500 IU, about 500 IU to about 2500 IU, about 750 IU to about 2500 IU, about 1000 IU to about 2500 IU, about 1 IU to about 1000 IU, about 100 IU to about 1000 IU, about 250 IU to about 1000 IU, about 500 IU to about 1000 IU, about 750 IU to about 1000 IU, or a range between any two values therein. Specific examples include, for example, about 500 IU, about 750 IU, about 800 IU, about 850 IU, about 900 IU, about 950 IU, about 1000 IU, about 1500 IU, about 2000 IU, about 2500 IU, about 5000 IU, about 10,000 IU, about 15,000 IU, about 20,000 IU or the like.

Vitamin B12, also called cobalamin, is a water soluble vitamin with a key role in the normal functioning of the brain and nervous system, and for the formation of blood. It may be normally involved in the metabolism of every cell of the human body, especially affecting DNA synthesis and regulation, fatty acid synthesis, and energy production. In some embodiments, the nutritional supplement may include vitamin B12. In some embodiments, vitamin B12 may be present in an effective amount from about 1 micrograms (mcg) to about 2000 mcg, from about 1 mcg to about 1500 mcg, from about 1 mcg to about 1000 mcg, from about 1 mcg to about 500 mcg, from about 1 mcg to about 300 mcg, from about 1 mcg to about 275 mcg, from about 1 mcg to about 100 mcg, from about 1 mcg to about 50 mcg, from about 1 mcg to about 30 mcg, from about 1 mcg to about 20 mcg, from about 1 mcg to about 10 mcg, from about 1 mcg to about 6 mcg, about 6 mcg to about 100 mcg, from about 6 mcg to about 75 mcg, from about 6 mcg to about 50 mcg, from about 6 mcg to about 40 mcg, from about 6 mcg to about 30 mcg, from about 6 mcg to about 20 mcg, from about 6 mcg to about 10 mcg, about 6, about 12 mcg, about 18 mcg, about 24 mcg, about 30 mcg, or a range between any two of these values. Specific examples include, for example, about 1000 mcg, about 750 mcg, about 500 mcg, about 300 mcg, about 275 mcg, about 250 mcg, about 225 mcg, about 200 mcg, about 150 mcg, or the like Resveratrol is a stilbenoid, a type of natural phenol, and a phytoalexin produced naturally by several plants that may lower blood sugar levels. Furthermore, without wishing to be bound by theory, resveratrol may also improve the autoimmune system, regulate weight, reduce inflammation, prevent certain forms of cancer, fight aging, and increase energy levels. Supplements of this compound will improve the overall health of individuals. Resveratrol may be found in, for example, red wine and may promote heart and cardiovascular health. In some embodiments, the nutritional supplement comprises resveratrol. In some embodiments, the resveratrol is in an effective amount from about 1 mg to about 4000 mg, about 1 mg to about 2000 mg, about 1 mg to about 1000 mg, about 1 mg to about 500 mg, about 1 mg to about 250 mg, about 1 mg to about 100 mg, about 1 mg to about 75 mg, about 1 mg to about 50 mg, about 1 mg to about 40 mg, about 1 mg to about 30 mg, about 1 mg to about 20 mg, about 5 mg to about 4000 mg, about 5 mg to about 2000 mg, about 5 mg to about 1000 mg, about 5 mg to about 500 mg, about 5 mg to about 250 mg, about 5 mg to about 100 mg, about 5 mg to about 75 mg, about 5 mg to about 50 mg, about 5 mg to about 40 mg, about 5 mg to about 30 mg, about 5 mg to about 20 mg, about 10 mg to about 500 mg, about 10 mg to about 250 mg, about 10 mg to about 100 mg, about 10 mg to about 75 mg, about 10 mg to about 50 mg, about 10 mg to about 40 mg, about 10 mg to about 30 mg, about 10 mg to about 20 mg, about 15 mg to about 500 mg, about 15 mg to about 250 mg, about 15 mg to about 100 mg, about 15 mg to about 75 mg, about 15 mg to about 50 mg, about 15 mg to about 40 mg, about 15 mg to about 30 mg, about 15 mg to about 20 mg, about 20 mg to about 500 mg, about 20 mg to about 250 mg, about 20 mg to about 100 mg, about 20 mg to about 75 mg, about 20 mg to about 50 mg, about 20 mg to about 40 mg, about 20 mg to about 30 mg, or a range between any two values therein. Specific examples include, for example, about 2000 mg, about 1500 mg, about 1000 mg, about 500 mg, about 100 mg, about 75 mg, about 50 mg, about 40 mg, about 30 mg, about 20 mg, about 15 mg or the like.

Piperine is derived from the fruits of black pepper. In some embodiments, piperine is BioPerine®. Without wishing to be bound by theory, it is believed that piperine may promote the bioavailability and absorption of various compounds. In particular, it is believed that piperine may promote the absorption of Coenzyme Q10, vitamins, minerals, herbals, amino acids, and the like. In some embodiments, the nutritional supplement composition may further comprise piperine. In some embodiments, the piperine may be in an effective amount from about 1 mg to about 500 mg, from about 1 mg to about 100 mg, from about 1 mg to about 75 mg, from about 1 mg to about 50 mg, from about 1 mg to about 25 mg, from about 1 mg to about 20 mg, from about 1 mg to about 15 mg, from about 10 mg, from about 1 mg to about 10 mg, from about 1 mg to about 5 mg, from about 5 mg to about 100 mg, from about 5 mg to about 75 mg, from about 5 mg to about 50 mg, from about 5 mg to about 25 mg, from about 5 mg to about 20 mg, from about 1 mg to about 15 mg, from about 10 mg, from about 5 mg to about 10 mg, about 15 mg, about 10 mg, about 5 mg, about 4 mg, about 3 mg, about 2 mg, about 1 mg, or ranges between any two of these values.

Vitamin B6 typically refers to pyridoxine, which is chemically known as 2-methyl-3-hydroxy-4,5-di(hydroxymethyl) pyridine and may also refer to pyridoxal or pyridoxamine. Pyridoxine, pyridoxal, and pyridoxamine may serve as precursors to pyridoxal-5'-phosphate (PLP), which is chemically known as 3-hydroxy-2-methyl-5-[(phosphonooxy)methyl]-4-pyridine-carboxaldehyde. For instance, mammals may produce PLP by phosphorylating pyridoxine by the action of pyridoxal kinase and then oxidizing the phosphorylated product. Without wishing to be bound by theory, it is believed that PLP is the biologically active form of vitamin B6 inside cells and in blood plasma. PLP is believed to be a regulator of biological processes and a cofactor in more than one hundred enzymatic reactions. PLP has been shown to be an antagonist of a purinergic receptors, thereby affecting ATP binding. Further, PLP has been implicated in modulating platelet aggregation, inhibiting certain phosphatase enzymes, and controlling gene transcription. The role of pyridoxal-5'-phosphate, and its precursors pyridoxal and pyridoxine (vitamin B6), in mediating cardiovascular health and in treating cardiovascular related diseases is disclosed. PLP may also be a coenzyme in certain enzyme-catalyzed processes, for example, in glycogenolysis, in malate-aspartate shuttle, and in homocysteine metabolism. In some embodiments, vitamin B6 may be in an effective amount from about 1 mg to about 2000 mg, from about 1 mg to about 1500 mg, from about 1 mg to about 1000 mg, about 1 mg to about 500 mg, from about 1 mg to about 100 mg, from about 1 mg to about 75 mg, from about 1 mg to about 50 mg, from about 1 mg to about 25 mg, from about 1 mg to about 20 mg, from about 1 mg to about 15 mg, from about 1 mg to about 10 mg, from about 1 mg to about 5 mg, from about 5 mg to about 2000 mg, from about 5 mg to about 1500 mg, from about 5 mg to about 1000 mg, from about 5 mg to about 500 mg, from about 5 mg to about 100 mg, from about 5 mg to about 75 mg, from about 5 mg to about 50 mg, from about 5 mg to about 25 mg, from about 5 mg to about 20 mg, from 5 mg to about 15 mg, from about 5 mg to about 10 mg, about 100 mg, about 50 mg, about 40 mg, about 30 mg, about 20 mg, about 10 mg, about 5 mg, about 4 mg, about 3 mg, about 2 mg, about 1 mg, or ranges between any two of these values.

Folic acid, also known as vitamin B9, is essential for various cellular functions such as DNA synthesis, DNA repair and is a cofactor for various biological reactions. Without wishing to be bound by theory, deficiency in folic acid may result in diarrhea, macrocytic anemia with weakness or shortness of breath, development defects in the embryos and behavioral disorders. In some embodiments, the nutritional supplement composition may further comprise folic acid. In some embodiments, the folic acid may be present in an effective amount from about 1 mcg to about 10,000 mcg, about 1 mcg to about 5,000 mcg, about 1 mcg to about 2000 mcg, about 1 mcg to about 1500 mcg, about 10 mcg to about 1250 mcg, about 50 mcg to about 10,000 mcg, about 50 mcg to about 5,000 mcg, about 50 mcg to about 1000 mcg, about 100 mcg to about 1000 mcg, about 150 mcg to about 1000 mcg, about 200 mcg to about 1000 mcg, about 250 mcg to about 1000 mcg, about 300 mcg to about 1000 mcg, about 1 mcg to about 500 mcg, about 10 mcg to about 500 mcg, about 50 mcg to about 500 mcg, about 100 mcg to about 500 mcg, about 150 mcg to about 500 mcg, about 200 mcg to about 500 mcg, about 250 mcg to about 500 mcg, about 300 mcg to about 500 mcg, about 1 mcg to about 300 mcg, about 10 mcg to about 300 mcg, about 50 mcg to about 300 mcg, about 100 mcg to about 300 mcg, about 150 mcg to about 300 mcg, about 200 mcg to about 300 mcg, about 250 mcg to about 300 mcg, about 10 mcg to about 5000 mcg, about 50 mcg to about 5000 mcg, about 100 mcg to about 5000 mcg, about 150 mcg to about 5000 mcg, about 200 mcg to about 5000 mcg, about 250 mcg to about 5000 mcg or a range between any two values therein. Specific examples include, for example, about 5,000 mcg, about 2000 mcg, about 1000 mcg, about 1250 mcg, about 1000 mcg, about 900 mcg, about 800 mcg, about 600 mcg, about 550 mcg, about 525 mcg, about 500 mcg, about 450 mcg, about 100 mcg, about 150 mcg, about 200 mcg, about 250 mcg, about 300 mcg, or the like.

In some embodiments, the nutritional supplement comprises each ingredient in an effective amount. In some embodiments, the nutritional supplement composition comprises each ingredient in an Estimated Average Requirement amount. The Estimated Average Requirements (EAR), is the amount expected to satisfy the dietary needs of 50% of the people in that age group based on a review of the scientific literature. In some embodiments, the nutritional supplement composition comprises each ingredient in an Recommended Dietary Allowance amount. Recommended Dietary Allowances (RDA), the daily dietary intake level of a nutrient considered sufficient by the Food and Nutrition Board to meet the requirements of nearly all (97-98%) healthy individuals in each life-stage and gender group. In some embodiments, the nutritional supplement composition comprises each ingredient in an Adequate Intake amount. Adequate Intake (AI), where no RDA has been established, but the amount established is somewhat less firmly believed to be adequate for everyone in the demographic group. In some embodiments, the nutritional supplement composition comprises each ingredient in an tolerable upper intake amount. Tolerable upper intake levels (UL), is the highest level of consumption that current data have shown to be safe for humans.

In some embodiments, the pharmaceutical excipient may include, without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. In some embodiments, the nutritional supplement composition may include an enteric coating.

In some embodiments, the nutritional supplement composition may further comprise other ingredients, such as, for example, other vitamins, herbs, hormones, minerals or essential fatty acids, to promote cardiovascular, heart, bone, or liver health. For example, in some embodiments, the nutritional supplement may further comprise acai, calcium, biotin, folic acid, vitamin A, curcumin, vitamin B12, piperine, fish oil, carotene, magnesium, potassium, zinc, lipase, amylase, or the like.

Some embodiments of the present disclosure are directed to a method of promoting nutritional health comprising administering to a subject in need thereof, a nutritional supplement composition including effective amounts of Coenzyme Q10, flax seed oil and/or borage oil, evening primrose oil, vitamin E, vitamin D, resveratrol and a pharmaceutically acceptable excipient. In some embodiments, the nutritional supplement may further comprise vitamin B12, piperine, fish oil or a combination thereof. In some embodiments, the nutritional supplement may be administered in conjunction with a drug that causes nutrient depletion. In some embodiments, the nutritional supplement may be administered in conjunction with a cholesterol lowering drug. In some embodiments, the nutritional supplement may be administered in conjunction with a blood pressure lowering drug. In some embodiments, the nutritional supplement may be administered in conjunction with a statin. In some embodiments, the nutritional supplement may be administered in conjunction with a beta-blocker. In some embodiments, the nutritional supplement may be administered in conjunction with statins, beta-blockers or a combination thereof.

Some embodiments of the present disclosure are directed to a method of promoting nutritional health comprising administering to a subject in need thereof a nutritional supplement composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient. In some embodiments, the nutritional supplement may be administered in conjunction with a drug that causes nutrient depletion. In some embodiments, the nutritional supplement may be administered in conjunction with a cholesterol lowering drug. In some embodiments, the nutritional supplement may be administered in conjunction with a blood pressure lowering drug. In some embodiments, the nutritional supplement may be administered in conjunction with a statin. In some embodiments, the nutritional supplement may be administered in conjunction with a beta-blocker. In some embodiments, the nutritional supplement may be administered in conjunction with statins, beta-blockers or a combination thereof.

Some embodiments of the present disclosure are directed to a method of promoting nutritional health comprising administering to a subject in need thereof a nutritional supplement composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient. In some embodiments, the nutritional supplement may be administered in conjunction with a drug that causes nutrient depletion. In some embodiments, the nutritional supplement may be administered in conjunction with a cholesterol lowering drug. In some embodiments, the nutritional supplement may be administered in conjunction with a blood pressure lowering drug. In some embodiments, the nutritional supplement may be administered in conjunction with a statin. In some embodiments, the nutritional supplement may be administered in conjunction with a beta-blocker. In some embodiments, the nutritional supplement may be administered in conjunction with statins, beta-blockers or a combination thereof.

In some embodiments, a method of promoting the efficacy of a statin comprises administering to a subject in need thereof a nutritional composition comprising Coenzyme Q10, flax seed oil and/or borage oil, evening primrose oil, vitamin E, vitamin D, resveratrol and a pharmaceutically acceptable excipient in conjunction with the statin. In some embodiments, the nutritional supplement may further comprise vitamin B12, piperine, fish oil or a combination thereof. In some embodiments, a method of promoting the efficacy of a statin comprises administering to a subject in need thereof, a nutritional composition consisting essentially of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient in conjunction with the statin. In some embodiments, a method of promoting the efficacy of a statin comprises administering to a subject in need thereof a nutritional composition consisting of Coenzyme Q10, flax seed oil and/or borage oil, evening primrose oil, vitamin D, resveratrol, fish oil, vitamin B6, vitamin E, folic acid, vitamin B12, piperine and a pharmaceutically acceptable excipient in conjunction with the statin. Without wishing to be bound by theory, it is believed that flax seed oil and/or borage oil which includes, without limitation, α-linolenic acid (ALA), eicosapentaenoic acid (EPA), docosahexaenoic acid (DHA), omega-6 fatty acids, omega-9 fatty acids and vitamin E, in combination with the other ingredients of the nutritional supplement compositions disclosed herein may increase the effectiveness of a statin and may cause a decline in cholesterol and aid in preventing myocardial infarctions and strokes.

In some embodiments, a method of alleviating male sexual dysfunction comprises administering a nutritional supplement composition of embodiments herein. Without wishing to be bound by theory, it is believed that piperine in combination with the other ingredients of the nutritional supplement compositions disclosed herein may help alleviate male sexual dysfunction. In some embodiments, the nutritional health supplement composition may be administered in conjunction with a beta-blocker.

In some embodiments, a method of preventing the oxidation of low-density lipoproteins (LDL) comprises administering a nutritional supplement composition of embodiments herein. Without wishing to be bound by theory, it is believed that oxidized LDL is detrimental to overall health.

In some embodiments, a method of promoting muscle health comprises administering a nutritional supplement composition of embodiments herein. In some embodiments, a method of promoting brain health comprises administering a nutritional supplement composition of embodiments herein. In some embodiments, a method of promoting bone health comprises administering a nutritional supplement composition of embodiments herein. In some embodiments, a method of promoting kidney health comprises administering a nutritional supplement composition of embodiments herein. In some embodiments, a method of promoting eye health comprises administering a nutritional supplement composition of embodiments herein. In some embodiments, the nutritional health supplement composition may be administered in conjunction with a statin, a beta-blocker, a blood pressure lowering medication, or a cholesterol lowering medication.

In some embodiments, a method of alleviating muscle soreness comprises administering a nutritional supplement composition of embodiments herein. In some embodiments, a method of alleviating muscle weakness comprises administering a nutritional supplement composition of embodiments herein. In some embodiments, a method of alleviating muscle pain comprises administering a nutritional supplement composition of embodiments herein.

Without wishing to be bound by theory, it is believed that mental confusion and memory loss may be caused by reduced high-density lipoprotein levels. In some embodiments, a method of normalizing high density lipoprotein levels comprises administering a nutritional supplement composition of embodiments herein. In some embodiments, a method of alleviating mental confusion comprises administering a nutritional supplement composition of embodiments herein. In some embodiments, a method of alleviating lethargy comprises administering a nutritional supplement composition of embodiments herein.

In some embodiments, a method of increasing energy comprises administering a nutritional supplement composition of embodiments herein. In some embodiments, a method of increasing stamina comprises administering a nutritional supplement composition of embodiments herein. In some embodiments, a method of increasing overall health comprises administering a nutritional supplement composition of embodiments herein. In some embodiments, a method of normalizing nutrient levels comprises administering a nutritional supplement composition of embodiments herein. In some embodiments, the nutritional health supplement composition may be administered in conjunction with a statin, a beta-blocker, a blood pressure lowering medication, or a cholesterol lowering medication.

The compounds of the present invention can be administered in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal or human being treated, age, weight, health, types of concurrent treatment, if any, and frequency of treatments, and can be easily determined by one of skill in the art (e.g., by the clinician).

Nutraceutical formulations containing the compounds of the present invention and a suitable carrier can be solid dosage forms which include, but are not limited to, softgels, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. In some embodiments, a single dose may comprise one or more softgels, tablets, capsules, cachets, pellets, pills, or the like. Specific examples include, for example, a dose comprising 1, 2, 3, or 4 softgels, tablets, capsules, cachets, pellets, pills or the like.

In some embodiments, one or more softgels, tablets, capsules, cachets, pellets, pills, or the like can be taken to achieve the desired dosing. In some embodiments, one or more softgels, tablets, capsules, cachets, pellets, pills, or the like can be taken simultaneously to achieve the desired dosing. In yet another embodiment one or more softgels, tablets, capsules, cachets, pellets, pills, or the like can be taken separately during the course of a specified time period such as for example, a 24 hour period. For example, one or more softgels, tablets, capsules, cachets, pellets, pills, or the like can be taken twice in a 24 hour period to achieve the desired dose. In some embodiments, one or more softgels, tablets, capsules, cachets, pellets, pills, or the like can be taken with a meal. For example one or more softgels, tablets, capsules, cachets, pellets, pills, or the like can be taken with each meal during the course of a 24 hour period to achieve the desired dose.

It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compositions of the present invention can also be formulated in rectal compositions such as suppositories or retention enemas, e.g., containing conventional suppository bases such as cocoa butter or other glycerides.

In addition to the formulations described previously, the compositions of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compositions of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

This invention and embodiments illustrating the method and materials used may be further understood by reference to the following non-limiting examples.

EXAMPLE 1

Softgel Formulation

A nutritional supplement packaged as a softgel capsule was prepared, with each softgel containing: 100 mg of Coenzyme Q10, 300 mg of 30% fish oil (180 mg EPA/120 mg DHA), 400 mg of evening primrose oil, 400 mg of flax seed oil, 40 IU of natural vitamin E, 1000 IU of vitamin D, and 20 mg of resveratrol.

EXAMPLE 2

Softgel Formulation

A nutritional supplement packaged as a softgel capsule was prepared, with each softgel containing: 150 mg of Coenzyme Q10, 1000 mg of 40/20 fish oil (400 mg EPA/200 mg DHA and 400 mg of other omega 3 fatty acids), 400 mg of evening primrose oil, 400 mg of flax seed oil, 10 IU of natural vitamin E, 2000 IU of vitamin D, and 50 mg of resveratrol.

EXAMPLE 3

Softgel Formulation

A nutritional supplement packaged as a softgel capsule was prepared, with each softgel containing: 150 mg of Coenzyme Q10, 1000 mg of 40/20 fish oil (400 mg EPA/200 mg DHA and 400 mg of other omega 3 fatty acids), 400 mg of evening primrose oil, 400 mg of flax seed oil, 10 IU of natural vitamin E, 2000 IU of vitamin D, 50 mg of resveratrol, 50 mg of vitamin B6, 250 mcg of vitamin B12 and 800 mcg of folic acid. The formulation may also include 160 mg of glycerol, 200 mg of enteric coating, 20 mg of beeswax, 60 mg of purified water and 29.15 mg of soybean oil. Recommended directions for use are to take one (1) softgel capsules daily, preferably with food.

EXAMPLE 4

Softgel Formulation

A nutritional supplement packaged as two softgel capsules was prepared, with each softgel containing: 75 mg of Coenzyme Q10, 500 mg of 40/20 fish oil (200 mg EPA/100 mg DHA and 200 mg of other omega 3 fatty acids), 200 mg of evening primrose oil, 200 mg of flax seed oil, 5 IU of natural vitamin E, 1,000 IU of vitamin D, 25 mg of resveratrol, 25 mg of vitamin B6, 125 mcg of vitamin B12 and 400 mcg of folic acid. The formulation may also include 80 mg of glycerol, 100 mg of enteric coating, 10 mg of beeswax, 30 mg of purified water and 14.575 mg of soybean oil. Recommended directions for use are to take two (2) softgel capsules daily, preferably with food.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A nutritional supplement composition consisting of about 150 mg coenzyme Q10, about 1000 mg of 40/20 fish oil (400 mg EPA/200 mg DHA and 400 mg of other omega 3 fatty acids), about 400 mg of evening primrose oil, about 400 mg of flaxseed oil, about 2000 IU of vitamin D, about 50 mg of resveratrol, about 50 mg of vitamin B6, about 250 mcg of vitamin B12, about 800 mcg of folic acid, gelatin, glycerin, beeswax, soybean oil, purified water, vitamin E, and food coloring.

2. The composition of claim 1, wherein the coenzyme Q10 is ubiquinone, ubiquinol or a combination thereof.

3. The composition of claim 1, wherein the composition is enteric coated.

4. The composition of claim 1, wherein the vitamin E is natural vitamin E.

5. The composition of claim 1, wherein the vitamin E is in an amount of about 10 IU.

6. The composition of claim 1, wherein the composition is formulated into a softgel.

7. The nutritional supplement composition of claim 1, wherein the nutritional supplement composition is capable of reducing the side effects of cholesterol lowering drugs.

8. The nutritional composition of claim 1, wherein the nutritional supplement composition is formulated for ameliorating nutrient depletion in a subject taking a cholesterol lowering drug.

9. The nutritional supplement composition of claim 1, wherein the nutritional supplement composition is in two unit doses.

10. A nutritional supplement composition consisting of about 75 mg of coenzyme Q10, 500 mg of 40/20 fish oil (200 mg EPA/100 mg DHA and 200 mg of other omega 3 fatty acids), 200 mg of evening primrose oil, 200 mg of flax seed oil, 5 IU of natural vitamin E, 1,000 IU of vitamin D, 25 mg of resveratrol, 25 mg of vitamin B6, 125 mcg of vitamin B12, 400 mcg of folic acid, gelatin, glycerin, beeswax, soybean oil, purified water, vitamin E, and food coloring.

11. The composition of claim 10, wherein the coenzyme Q10 is ubiquinone, ubiquinol or a combination thereof.

12. The composition of claim 10, wherein the composition is an enteric coated softgel.

* * * * *